United States Patent
Jiang et al.

(10) Patent No.: US 9,732,040 B2
(45) Date of Patent: Aug. 15, 2017

(54) LOW 4-METHYLIMIDAZOLE (4-MEI) CARAMEL COLOR CLASS IV PRODUCTION

(71) Applicants: Hongxin Jiang, Bridgewater, NJ (US); Felipe Torres Diaz, Guadalajara (MX); Brad Carnish, Somerset, NJ (US); Jose Angel Contreras, Guadalajara (MX); Juan Carlos Rico, Guadalajara (MX); Jesus Adrian Guerra Martinez, Queretaro (MX)

(72) Inventors: Hongxin Jiang, Bridgewater, NJ (US); Felipe Torres Diaz, Guadalajara (MX); Brad Carnish, Somerset, NJ (US); Jose Angel Contreras, Guadalajara (MX); Juan Carlos Rico, Guadalajara (MX); Jesus Adrian Guerra Martinez, Queretaro (MX)

(73) Assignee: Corn Products Development, Inc., Sao Paulo (BR)

( * ) Notice: Subject to any disclaimer, the term of this patent is extended or adjusted under 35 U.S.C. 154(b) by 160 days.

(21) Appl. No.: 14/170,048

(22) Filed: Jan. 31, 2014

(65) Prior Publication Data

US 2016/0221961 A1  Aug. 4, 2016

(51) Int. Cl.
*C07D 233/58* (2006.01)
*B01J 27/24* (2006.01)
*B01J 27/02* (2006.01)

(52) U.S. Cl.
CPC ............ *C07D 233/58* (2013.01); *B01J 27/24* (2013.01)

(58) Field of Classification Search
CPC .......... C07D 233/58; B01J 27/24; B01J 27/02
USPC ..................................................... 548/335.1
See application file for complete search history.

(56) References Cited

U.S. PATENT DOCUMENTS

| | | |
|---|---|---|
| 2,582,261 A | 1/1952 | Longenecker |
| 2,784,118 A | 3/1957 | Pyle et al. |
| 4,138,271 A | 2/1979 | Ohira et al. |
| 4,416,700 A | 11/1983 | Clark et al. |
| 4,614,662 A | 9/1986 | Ramaswamy |
| 4,803,281 A | 2/1989 | Mesch |
| 2010/0003383 A1 | 1/2010 | Parker et al. |
| 2011/0244102 A1 | 10/2011 | Ramaswamy et al. |
| 2011/0250338 A1 | 10/2011 | Ramaswamy et al. |

FOREIGN PATENT DOCUMENTS

| | | | |
|---|---|---|---|
| EP | 0212049 A2 | 4/1987 | |
| WO | WO 2010002723 A1 * | 1/2010 | ............... A23G 3/32 |

OTHER PUBLICATIONS

J.Jakovljevic, T. Odadzic and J. Sakac—Synthesis and Properties of Caramel on a Starch Hydrolysate Basis—Zbornik Radova No. 22/1991 (pp. 7-11), Faculty of Technolog, NOVI SAD.
W. Kamuf, A. Nixon, O. Parker, and G. C. Barnum, Jr.—D.D. Williamson Louisville, KY—Overview of Caramel Colors—Publication No. W-2003-0205-01F—(c) 2003 American Association of Cereal Chemists, Inc.—64/Mar.-Apr. 2003, vol. 48, No. 2.
Caramel Color—Wikipedia, the Free Encyclopedia—Oct. 23, 2013.

* cited by examiner

*Primary Examiner* — Matthew Coughlin
*Assistant Examiner* — Sagar Patel
(74) *Attorney, Agent, or Firm* — Jacqueline Cohen; Jason Grauch

(57) ABSTRACT

The application pertains to a process comprising a) acidifying a carbohydrate to a pH below 2; b) heating the mixture from step a) to a temperature from about 60° C. to about 100° C.; c) adding a catalyst to the mixture from step b) over a time from about 10 minutes to about 200 minutes; d) heating the mixture from step c) to a temperature from about 121° C. to about 140° C. and to a pressure of about 4.5 Kg/cm$^2$ to about 5.3 Kg/cm$^2$ over a time from about 15 minutes to about 90 minutes; and e) maintaining the mixture of step d) at a temperature from about 121° C. to about 140° C. and a pressure of about 4.5 Kg/cm$^2$ to about 5.3 Kg/cm$^2$ over a time from about 1 minute to about 300 minutes.

17 Claims, 1 Drawing Sheet

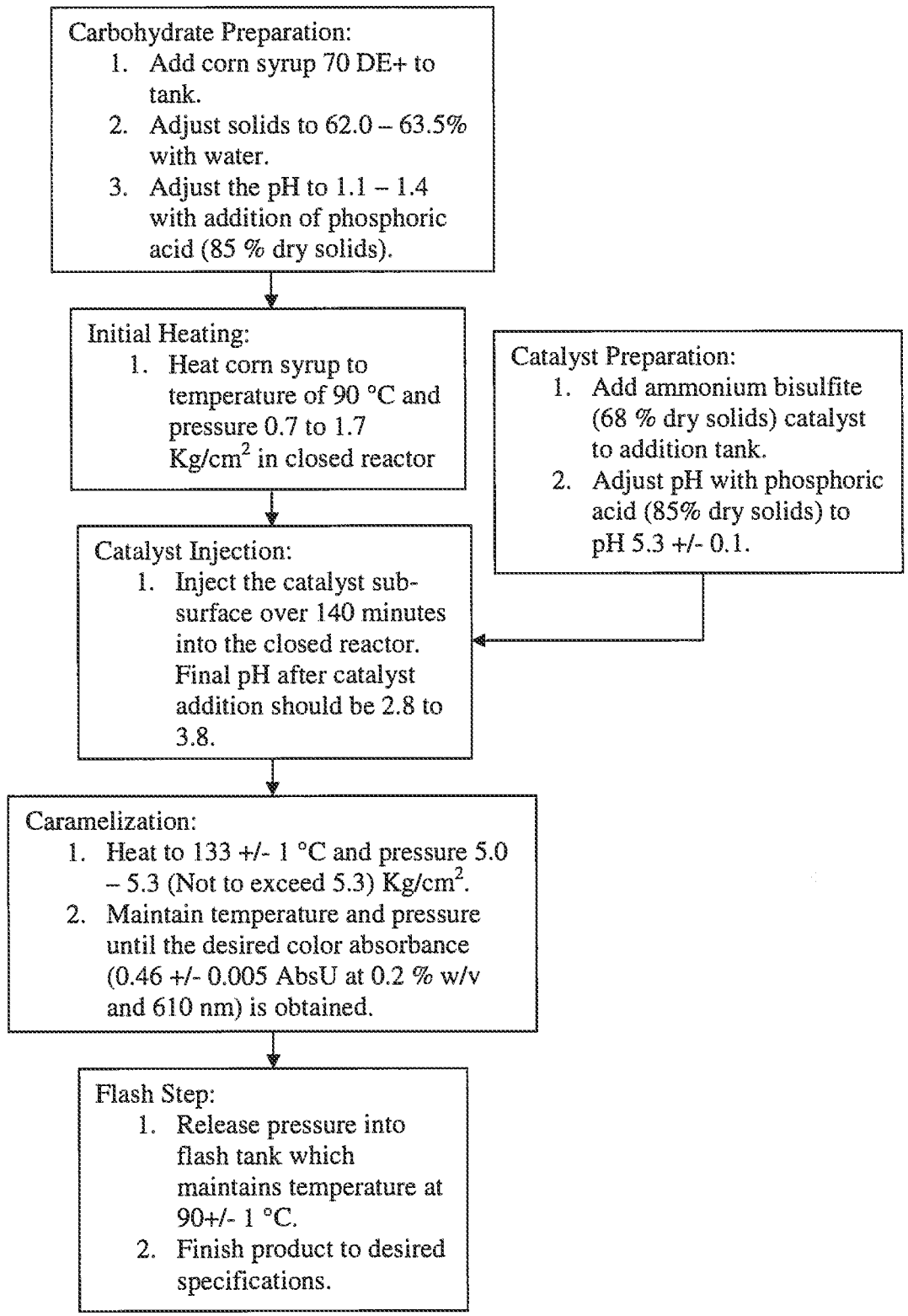

LOW 4-METHYLIMIDAZOLE (4-MEI) CARAMEL COLOR CLASS IV PRODUCTION

BACKGROUND

4-Methylimidazole (1) is a heterocyclic organic chemical compound formed in the browning of certain foods through the Maillard reaction between carbohydrates and nitrogen compounds. It is found in roasted foods, grilled meats, coffee, and in types of caramel color produced with ammonia-based processes. Scheme 1 sets forth the likely reactions taking place during the caramel color production process.

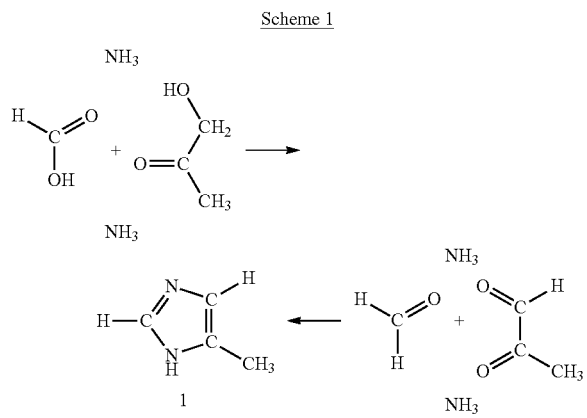

Scheme 1

Caramel color is one of the oldest and most widely-used food colorings, and is found in almost many commercially produced foods. Caramel color is manufactured by heating carbohydrates, alone or in the presence of acids, bases, and/or salts. There are four classes of caramel color, classified according to the reactants used in their manufacture, each with its own Class and INS, as listed in Table 1.

TABLE 1

| Class | INS No. | Name | Preparation | Uses |
|---|---|---|---|---|
| I | 150a | Plain caramel | No ammonium or sulfite compounds used | Whiskey and other high proof alcohols |
| II | 150b | Caustic sulfite caramel | Sulfite compounds but no ammonium compounds used | Cognac, sherry and some vinegars |
| III | 150c | Ammonia caramel, baker's caramel, confectioner's caramel, or beer caramel | Ammonium compounds but no sulfite compounds used | Beer, sauces, and confectionery |
| IV | 150d | Sulfite ammonia caramel, acid-proof caramel, or soft-drink caramel | Both sulfite and ammonium compounds | Acidic environments including soft drinks |

Caramel coloring of all types are considered safe and are approved by many leading regulatory agencies around the world, such as the European Food Safety Authority (USA), the US Food and Drug Administration (FDA), and the Joint FAO/WHO Expert Committee on Food Additives (JECFA).

SUMMARY

The application pertains to a process comprising a) acidifying a carbohydrate to a pH below 2; b) heating the mixture from step a) to a temperature from about 60° C. to about 100° C.; c) adding a catalyst to the mixture from step b) over a time from about 10 minutes to about 200 minutes; d) heating the mixture from step c) to a temperature from about 121° C. to about 140° C. and to a pressure of about 4.5 Kg/cm$^2$ to about 5.3 Kg/cm$^2$ over a time from about 15 minutes to about 90 minutes; and e) maintaining the mixture of step d) at a temperature from about 121° C., to about 140° C. and a pressure of about 4.5 Kg/cm$^2$ to about 5.3 Kg/cm$^2$ over a time from about 1 minute to about 300 minutes. As used herein, dextrose equivalent (DE) of a hydrolysis product is defined as its reducing power as a percentage of the reducing power of pure dextrose. DE may be calculated using the formula:

$$\text{Dextrose equivalent } ref. \text{ available} = \frac{\text{milligrams of reducing sugar as dextrose} \times 100}{\text{milligrams of dry substance}}$$

Each starch molecule has one reducing end: therefore DE is inversely related to molecular weight. The DE of anhydrous D-glucose is defined as 100 and the DE of unhydrolyzed starch is virtually zero.

BRIEF DESCRIPTION OF THE DRAWING

FIG. 1 depicts a process flow diagram of the caramel color process.

DETAILED DESCRIPTION

The application pertains to a process comprising a) acidifying a carbohydrate to a pH below 2; b) heating the mixture from step a) to a temperature from about 60° C. to about 100° C.; c) adding a catalyst to the mixture from step b) over a time from about 10 minutes to about 200 minutes; d) heating the mixture from step c) to a temperature from about 121° C. to about 140° C. and to a pressure of about 4.5 Kg/cm$^2$ to about 5.3 Kg/cm$^2$ over a time from about 15 minutes to about 90 minutes; and e) maintaining the mixture of step d) at a temperature from about 121° C. to about 140° C. and a pressure of about 4.5 Kg/cm$^2$ to about 5.3 Kg/cm$^2$ over a time from about 1 minute to about 300 minutes.

The carbohydrate may be derived from any native source, any of which may be suitable for use herein. Typical sources for the carbohydrate are cereals, tubers, roots, legumes and fruits. The carbohydrate may be refined derived from common sources of sugars such as sugar cane and sugar beet. They may also be derived by processes known in the art from native sources of starch such as varieties of corn (maize), pea, potato, sweet potato, banana, barley, wheat, rice, oat, sago, amaranth, tapioca (cassava), arrowroot, canna, and sorghum.

In one embodiment, the carbohydrate is a carbohydrate syrup, and in another embodiment, a corn syrup, wheat syrup, or mixtures thereof. In one aspect of the invention, the dextrose equivalent of the carbohydrate is 70 or greater and in another aspect is 80 or greater. If the carbohydrate used is in dry form, the carbohydrate should be mixed into solution (water) prior to use. In one embodiment, the carbohydrate used is in a solution of at least about 30 Baume and in another of at least 35 Baume.

The pH of the carbohydrate is decreased using methods known in the art. In one embodiment, an inorganic acid is used, and in another embodiment, the acid is selected from the group consisting of hydrochloric acid, sulfuric acid, sulfurous acid, sodium metabisulfite and phosphorous based acids, in particular phosphorus and phosphoric acid. In one suitable embodiment, the pH of the carbohydrate is decreased using phosphoric acid.

In an embodiment, the pH in step (a) is decreased to greater than or equal to 1 and in another embodiment greater than or equal to 1.1. In an embodiment, the pH in step (a) is no greater than 2, and in another embodiment no greater than 1.5.

The acidified carbohydrate is then heated. In an embodiment, the temperature in this step (b) is greater than or equal to 60° C. and in another embodiment is greater or equal to 85° C. In an embodiment, the temperature in this step (b) is no greater than 100° C. and in another embodiment, no greater than 95° C.

Subsequent to reaching temperature, the catalyst is added to the acidified carbohydrate. In one embodiment, the catalyst is ammonium bisulfite. The pH of the catalyst and/or the pH of the blend of acidified carbohydrate and catalyst may be adjusted as necessary using standard methods known in the art. For example, if the pH is to be adjusted upwards, an alkali such as potassium hydroxide or sodium hydroxide may be used. If the pH is to be adjusted downwards, an acid may be used, such as the acids used to acidify the carbohydrate.

In one embodiment, the catalyst is added by injecting it below the surface of the acidified carbohydrate (subsurface).

In one embodiment, the ratio of carbohydrate used in step (a) to that of the ammonium bisulfite used in step (b) is at least 1 to 3 to about 1 to 5 (w/w dry basis). In another embodiment, the ratio of corn syrup used in step a) to that of the ammonium bisulfite used in step b) ranges from about 1 to 3.5 to about 1 to 4.5 (w/w db). In another embodiment, the ratio of corn syrup used in step a) to that of the ammonium bisulfite used in step b) ranges from about 1 to 4 to about 1 to 4.4 (w/w db).

The catalyst is added gradually (as opposed to in a single dosage) over a period of time from about 10 minutes to about 200 minutes while maintaining the temperature from about 60° C. to about 100° C. In one embodiment, the addition time in step (c) is at least 10 minutes. In one embodiment, the addition time in step (c) is no more than 200 minutes, an another no more than 140 minutes, in yet another embodiment no more than 100 minutes, in still yet another embodiment no more than 70 minutes, in a still further embodiment, no more than 35 minutes, and in a further embodiment, no more than 25 minutes.

Over the next about 15 to about 90 minutes, the temperature is raised to from about 121° C. to about 140° C. and the pressure is raised to a pressure of about 4.5 Kg/cm$^2$ to about 5.3 Kg/cm$^2$. In one embodiment, the temperature is raised to at least 121° C., and in another embodiment to at least 130° C. In one embodiment, the temperature is raised to no greater than 140° C. and in another embodiment to no greater than 135° C. In one embodiment, the pressure is raised to at least 4.5 Kg/cm$^2$ and in another embodiment to at least 4.8 Kg/cm$^2$. In one embodiment the pressure is raised to no greater than 5.3 Kg/cm$^2$.

The pressure and temperature of step (d) is maintained until the desired caramel coloring is produced. In one embodiment, the time in step (e) is at least 1 minute. In an embodiment, the time of step (e) is no more than 200 minutes, and in another embodiment no more than 150 minutes, in yet another embodiment no more than 75 minutes, in still yet another embodiment no more than 40 minutes, and in a still further another embodiment no more than 20 minutes.

Once the desired caramel color is obtained, the pressure is released to ambient pressure. In one embodiment, the temperature is decreased with the reduction of pressure to a temperature of no more than about 100° C. and in another embodiment to a temperature of no more than 90° C.

The resultant caramel color may be adjusted using standard methods known in the art. The degree Baume and/or pH may be adjusted.

The resultant caramel color obtained by this process has a viscosity of less than 500 cps measured at 23° C. In another embodiment, the viscosity of the resultant caramel color obtained by this process is less than 200 cps measured at 23° C. In yet another embodiment, the viscosity of the resultant caramel color obtained by this process is less than 100 cps measured at 23° C. Viscosity, as used herein, is measured by Brookfield Viscometer using the analytical procedure set forth in the Examples section and is measured on caramel color adjusted to a Baume of 30.0-31.0 at 15.5° C.

In one embodiment, the viscosity of caramel color obtained by this process is stable at a storage temperature of 40° C. for at least 8 weeks, and in another embodiment, the viscosity of caramel color obtained by this process is stable at a storage temperature of 40° C., for at least 12 weeks. As used herein, a stable viscosity is one which changes by no more than 50 cps from the initial viscosity (that prior to storage).

The resultant caramel color can be of different color intensities depending upon the cooking time, temperature and catalyst concentration. In one embodiment, the caramel color at 0.1% (w/v) measured at 610 nm is at least 0.2 Uabs and in another embodiment is at least 0.21 Uabs. In one embodiment, the caramel color at 0.1% (w/v) measured at 610 nm is no more than 0.25 Tabs and in another embodiment is no more than 0.24 Uabs.

The resultant caramel color (at a Baume of 30.0-31.0 at 15.5° C.) has a 4-MeI content less than 20 ppm, in one embodiment less than 15 ppm, in another embodiment less than 10 ppm and in still yet another embodiment less than 5 ppm.

The ammonium bisulfite is gradually added to the caramelization reaction mixture rather than addition of ammonium bisulfite all at once. It is hypothesized that as this gradual additional of ammonium bisulfite will minimize the concentration of 4-MeI in the final caramel color product. Without being bound by theory, since the reactions to form 4-MeI require two equivalents of ammonia, if the rate of making 4-MeI is higher order in ammonia, then the lower the ammonia concentration during the process, the slower will be formation of 4-MeI at the expense of other compounds formed from only one equivalent of ammonia. Low concentrations of free ammonia may be achieved by slow addition of ammonium compounds during the reaction and by operating at slightly lower pH conditions.

EXAMPLES

Brookfield Viscosity Evaluation Procedure.

The viscosity and appearance of samples were assessed using a Brookfield Viscometer Model RV-DV-H+PRO, with standard needle and a laboratory support, and Fluid 100, which is a standard of calibration available of silicone of 100 cps (available from Brookfield Engineering Laboratories, Inc. 240. Cushing Stoughton Mass. 02072). About 500 mL of caramel color sample was pour into a 600 mL stainless steel vessel, sliding the vessel wall to prevent the formation of air bubbles. In a recirculating water bath at a controlled temperature, the container with the sample was placed to warm up to 30° C., verifying the temperature with the help of a digital or mercury thermometer. The viscometer was placed into the holder and adjusted to the proper height. The needle viscometer was carefully connected by holding the shaft tightly and screwing the needle to the left. The guard was positioned and assembly level. The guard and caramel color needle were introduced at an angle to prevent the formation of air bubbles. Adjusted the apparatus so that the notch was on the surface of the sample. The viscometer was started at 20 or 50 rpm and spindle number 1 or 2 used. The viscosity was read and reported.

Example 1

As shown in the process flow chart of FIG. 1, sugar carbohydrates are heated up in the presence of phosphoric acid to lower the pH to the range of 1.1-1.4. Catalyst is added under an injection model (sub-surface) to avoid loss of volatiles. The caramelization reaction is carried out under pressure at about 133° C. After completion of the reaction, the pressure is released as the product is transferred to another tank and adjusted for solids content. Analysis of final product shows 4-MeI values lower than 12 ppm.

Example 2—Manufacturing Procedure

1. Ammonium bisulfite solution (68% dry solids) was adjusted to a pH of 5.3±0.1 using phosphoric acid (85% dry solids).
2. The carbohydrate was prepared by blending in the preparation tank the corn syrup with water in the amounts specified in Table 2. The pH of this blend was about 4.0-5.5 and the dry solids content was between 62.0-63.5%.
3. The blend was thoroughly mixed at room temperature (20.0-30.0° C.) and the pH was adjusted as needed using phosphoric acid (85% dry solids) and/or potassium hydroxide to a pH between 1.1 to 1.4.
4. The pH and dry solid content were measured and recorded.

TABLE 2

| COMPONENT | Formula |
|---|---|
| | % Commercial Weight |
| Corn syrup DE = 70 (80-83% dry solids) | 62.68 |
| Catalyst (NH$_4$HSO$_3$ 68%) | 17.71 |
| Deionized Water | 19.60 |
| Total | 100 |

5. The syrup was loaded from the preparation tank into the reactor and agitation was started.
6. The targeted amount of phosphoric acid (H$_3$PO$_4$) at 85% dry solids to be used in step 1 and 2 combined is calculated by 2.12% w/w of the total reactor mass in step 5.
7. The syrup was heated to 90° C.±1° C. At this point pressure in the reactor would be 0.7-1.7 kg/cm$^2$.
8. The catalyst injection was set at a constant flow rate such that the full quantity of catalyst will be added in 140 minutes.
9. After the catalyst injection was completed, the reactor was allowed to thoroughly mix for 10 min, after which a sample was taken. The measured pH both during and after the catalyst injection was in the range of 2.8-3.8.
10. The temperature was increased to 133° C.±1° C.; the reaction was allowed to proceed at this temperature until the desired color absorbance of 0.46+/−0.005 AbsU at 0.2% (w/v) was obtained.
11. After the desired color absorbance was obtained, the reaction was stopped with a flash step.
12. As needed according to the product specifications, additional downstream processing was applied.

While particular embodiments of the present application have been illustrated and described, it would be obvious to those skilled in the art that various other changes and modifications can be made without departing from the spirit and scope of the application. It is therefore intended to cover in the appended claims all such changes and modifications that are within the scope of this application.

What is claimed is:

1. A process comprising:
   a) acidifying a carbohydrate to a pH below 2;
   b) heating the mixture from step a) to a temperature from about 60° C. to about 100° C.;
   c) adding a catalyst comprised of ammonium and sulfite compounds to the mixture from step b) over a time from about 10 minutes to about 200 minutes;
   d) heating the mixture from step c) to a temperature from about 121° C. to about 140° C. and to a pressure of about 4.5 Kg/cm$^2$ to about 5.3 Kg/cm$^2$ over a time from about 15 minutes to about 90 minutes; and
   e) maintaining the mixture of step d) at a temperature from about 121° C. to about 140° C. and a pressure of about 4.5 Kg/cm$^2$ to about 5.3 Kg/cm$^2$ over a time from about 1 minute to about 300 minutes to produce a caramel color having a concentration of 4-MeI of less than 20 ppm and a color intensity, at 0.1% (w/v) measured at 610 nm of at least 0.2 Uabs.

2. The process of claim 1, wherein the pH in step a) is from about 1.1 to about 1.4.

3. The process of claim 1, wherein the temperature in step b) is from about 87° C. to about 93° C.

4. The process of claim 3, wherein the temperature in step b) is from about 89° C. to about 91° C.

5. The process of claim 1, wherein the addition time in step c) is from about 10 minutes to about 70 minutes.

6. The process of claim 5, wherein the addition time in step c) is from about 10 minutes to about 25 minutes.

7. The process of claim 1, wherein the temperature in either step d) and/or step e) is from about 131° C. to about 134° C.

8. The process of claim 1, wherein the pressure in either step d) or step e) is from about 4.8 Kg/cm$^2$ to about 5.3 Kg/cm$^2$.

9. The process of claim 1, wherein the time in step e) is from about 1 minute to about 40 minutes.

10. The process of claim 1, wherein the carbohydrate of step a) is a corn syrup, and wherein the ratio of corn syrup used in step a) to that of the ammonium and sulfite compounds used in step b) ranges from about 1 to 3.5 to about 1 to 4.5 (w/w dry solids).

11. The process of claim 1, wherein the catalyst is added in step (c) by injecting it sub-surface to the mixture.

12. The process of claim 1, wherein the concentration of 4-MeI in the caramel color is less than 15 ppm.

13. The process of claim 12, wherein the concentration of 4-MeI in the caramel color is less than 10 ppm.

14. The process of claim 13, wherein the concentration of 4-MeI in the caramel color is less than 5 ppm.

15. The process of claim 1, wherein the caramel color has a viscosity of less than 500 cps measured at 23° C.

16. The process of claim 15, wherein the viscosity is stable at a storage temperature of 40° C. for at least 8 weeks.

17. A process comprising:
   a) acidifying a carbohydrate comprised of a corn syrup to a pH between about 1.1 and about 1.4;
   b) heating the mixture from step a) to a temperature from about 87° C. to about 93° C.;
   c) adding a catalyst comprised of ammonium bisulfite to the mixture from step b) over a time from about 10 minutes to about 200 minutes;
   d) heating the mixture from step c) to a temperature from about 130° C. to about 135° C. and to a pressure of about 4.5 Kg/cm$^2$ to about 5.3 Kg/cm$^2$ over a time from about 15 minutes to about 90 minutes; and
   e) maintaining the mixture of step d) at a temperature from about 130° C. to about 135° C. and a pressure of about 4.5 Kg/cm$^2$ to about 5.3 Kg/cm$^2$ over a time from about 1 minute to about 40 minutes to produce a caramel color having a concentration of 4-MeI of less than 5 ppm, a viscosity of less than 100 cps when measured at 23° C., and a color intensity at 0.1% (w/v) measured at 610 nm of between about 0.20 Uabs and about 0.24 Uabs; and
wherein, the ratio of corn syrup used in step a) to that of the ammonium and sulfite compounds used in step b) ranges from about 1 to 3.5 to about 1 to 4.5 (w/w dry solids).

* * * * *